United States Patent [19]
Fitzjarrell

[11] Patent Number: 5,989,523
[45] Date of Patent: Nov. 23, 1999

[54] TOPICAL SPRAY FOR TREATING ACNE CONTAINING NIACINAMIDE AND NAPCA

[76] Inventor: Edwin A. Fitzjarrell, 68994 N. Pine St., Sisters, Oreg. 97759

[21] Appl. No.: 09/044,978

[22] Filed: Mar. 20, 1998

[51] Int. Cl.⁶ ..................................................... A61K 9/12
[52] U.S. Cl. ........................... 424/45; 424/195.1; 424/46; 424/78.05; 424/78.07; 424/78.06; 514/937; 514/944; 514/859
[58] Field of Search ................................. 424/195.1, 45, 424/46, 78.05, 78.07, 78.06; 514/859, 944, 937

[56] References Cited

U.S. PATENT DOCUMENTS

| | | |
|---|---|---|
| 4,505,896 | 3/1985 | Bernstein . |
| 4,593,046 | 6/1986 | Gruber ..................................... 514/717 |
| 4,619,829 | 10/1986 | Motschan . |
| 4,725,609 | 2/1988 | Kull, Jr. et al. . |
| 4,743,442 | 5/1988 | Raaf et al. . |
| 4,900,550 | 2/1990 | Lowry . |
| 5,266,318 | 11/1993 | Taylor-McCord . |
| 5,449,512 | 9/1995 | Simmons . |
| 5,496,827 | 3/1996 | Patrick . |
| 5,520,919 | 5/1996 | Lerner . |
| 5,520,991 | 5/1996 | Eustatiu . |
| 5,527,530 | 6/1996 | Simmons et al. . |
| 5,556,887 | 9/1996 | Lerner . |

FOREIGN PATENT DOCUMENTS 964444  7/1964  United Kingdom .

OTHER PUBLICATIONS

Shalita, Alan, R.; et al., Topical Nicotinaminde Compared With Clindamycin Gel in the Treatment of Inflammatory Acne Vulgaris, Int. J. Dermatol., 1995, V. 34, pp. 434–437.

Syed, T. A., et al, Management of Psoriasis with Aloe vera Extract in a Hydrophilic Cream: a placebo–controlled, double blind study, Trop. Med. Int. Health, Aug., 1996 1(4) pp. 505–509.

Jablonska, M.D., Treatment of Acne Vulgaris and Rosacea, letter to the editor, *Arch. Dermatology*, vol. 111, Jul. 1975, p. 929.

Comaish, Topically Applied Niacinamide in Isoniazid–Induced Pellagra, *Arch. Dermatology*, vol. 112, Jan. 1976, pp. 70–72.

*Primary Examiner*—Raj Bawa
*Attorney, Agent, or Firm*—ipsolon llp

[57] ABSTRACT

A method and composition for treating outbreaks of acne. Initially, the acne affected area is cleaned. A topical spray comprising about 1 to 10 wt % niacinamide, about 0.1 to 1 wt % Aloe Vera extract and about 0.1 to 1 wt % NaPCA in a water carrier is then applied to the area. Generally, at least two spray applications are made each day. For optimum skin cleaning, an exfoliation scrub such as a conventional apricot facial scrub is preferably applied to the skin prior to application of the combination topical spray.

2 Claims, No Drawings

TOPICAL SPRAY FOR TREATING ACNE CONTAINING NIACINAMIDE AND NAPCA

FIELD OF THE INVENTION

This invention relates to topical spray for application to the skin for the treatment of acne.

BACKGROUND OF THE INVENTION

Acne is a skin disorder that occurs most commonly among teen-agers. It consists of various kinds of blemishes on the face, upper chest and back. Severe acne can result in scarring. Acne is most likely in the facial area extending from around the nose to around the chin. This area is also most visible and acne here can be very distressing to the victim.

During early adolescence, hormone production begins that stimulates the oil glands in the skin. These sebaceous glands grow larger and produce more oil. Each sebaceous gland empties into a hair follicle and passes to the skin through a pore. Sometimes the pores become plugged and oil accumulates under the plugs. Pimples and cysts, caused by the acne bacillus, become infected resulting in redness and pus. Cysts may leave permanent scars, as may pimples if squeezed or scratched. Mild acne can be treated with diet changes, careful washing and nonprescription lotions containing benzoyl peroxide, topical creams containing salicylic acid, or other medications. Vitamin A palmitate may be applied topically for the treatment of acne and other skin disorders as described by Lerner in U.S. Pat. Nos. 5,556,887 and 5,520,919. Severe acne may be treated with tetracycline, 13-cis-retinoic acid and other prescription drugs. The skin may be treated with acid or freezing in some cases to make the skin peel. These treatments are often unsuccessful and may have significant side effects. Often, at best, these treatments reduce the intensity or frequency of acne outbreaks.

The most difficult area for treating acne is a generally "O" or elliptical shaped area on the face that includes the nose and chin. Acne can also occur on other parts of the face, the shoulders, neck, etc.

Thus, there is a continuing need for methods and compositions for treating acne that are more effective in preventing flare-up of acne and in reducing or eliminating acne outbreaks that have begun and that have fewer side effects.

SUMMARY OF THE INVENTION

The above-noted problems, and others, are overcome in accordance with this invention by a novel medicated topical spray and a treatment method using that spray. The spray basically comprises a water carrier, preferably distilled water, niacinamide, Aloe Vera extract and NaPCA.

For optimum results, the skin is cleaned with an exfoliating scrub prior to applying the topical spray. Preferably, about 0.5 to 2 ml. Of the spray is applied to the central area of the face or to an equivalent other skin area during each treatment. This spray application is preferably done about twice each day.

The spray preferably comprises from about 1 to 10 wt % niacinamide in a carrier, such as water. For optimum results, about 5 wt % niacinamide is used.

From about 0.1 to 1 wt % Aloe Vera extract is included in the solution. Mild stinging has been reported with niacinamide used alone. The Aloe Vera extract has been found to eliminate this problem. In addition, the Aloe Vera extract appears to have a direct effect in severe acne, similar to its effectiveness in treating psoriasis vulgaris. For optimum effectiveness, about 0.5 wt % Aloe Vera extract is used.

Some patients may have problems with the water carrier drying their skin. The addition of from about 0.1 to 1 wt % NaPCA to the solution has been found to overcome this problem. The NaPCA is sodium salt of pyrrolidone carboxyic acid, which is an extremely hygroscopic natural humectant compound found in skin. In fact, patients have found that they no longer require a moisturizer at night once they began using the treatment of this invention. For optimum effectiveness, use of about 0.5 wt % NaPCA is preferred.

Any suitable scrub may be used when one is found desirable. Particularly effective scrubs include apricot facial scrubs of the sort available from Freeman and St. Ives.

It is, therefore, an object to provide an effective treatment for acne. A further object is to provide a treatment that reduces the incidence and severity of acne outbreaks. Still a further object is a treatment that avoid side effects.

DETAILED DESCRIPTION OF PREFERRED EMBODIMENTS

The topical spray solution is prepared by mixing niacinamide, Aloe Vera extract and NaPCA with any suitable inert carrier, such as water. Distilled water is preferred to avoid any contaminates or interfering agents that may be present in tap water.

Any suitable ratio of niacinamide to carrier may be used. From about 1 to 10 wt % niacinamide in the carrier has been found to be effective. For best results it is preferred that from about 5 grams niacinamide per 100 grams solution be used for optimum over all results.

About 0.1 to 1 wt % Aloe Vera extract has been found to be effective in overcoming any stinging effect of the niacinamide. A typical effective Aloe Vera extract useful in this invention is available from Aloe Laboratories, Inc. Optimum effectiveness has been found with about 0.5 wt % Aloe Vera extract.

From about 0.1 to 1 wt % NaPCA is mixed into the solution. This range has been found to be highly effective in preventing skin drying by the water carrier. For optimum effectiveness, about 0.5 wt % NaPCA is used.

Prior to use of the topical solution, the area affected by acne is preferably cleaned. Any suitable cleaning method may be used, typically using a suitable cleaning agent and water. For best results, it is preferred that an exfoliation scrub, such as a conventional apricot facial scrub, be used to assure skin cleanliness and to lightly abrade the skin.

After the skin is cleansed, the topical solution is sprayed on the area as indicated. In most cases, the central facial area covering the nose and chin is most in need of treatment. Any suitable spraying device may be used, such as conventional pump or aerosol sprayers. Typically, the skin will be cleansed and sprayed at least twice a day. The total of said solution applied is preferably about 3 ml/day.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A topical spray for treating acne, which comprises: an aqueous solution of from about 5 wt % niacinamide, 0.5 wt % Aloe Vera extract and about 0.5 wt % NaPCA.

2. A topical spray for treating acne, which comprises: an aqueous solution of from about 1 to 10 wt % niacinamide, about 0.1 to 1 wt % Aloe Vera extract, and about 0.1 to 1 wt % NaPCA.

* * * * *